(12) United States Patent
Maruyama et al.

(10) Patent No.: US 11,675,887 B2
(45) Date of Patent: Jun. 13, 2023

(54) MOVEMENT HISTORY INFORMATION CONFIRMING METHOD, SYSTEM THEREFOR, AND MANAGEMENT SERVER

(71) Applicant: PATIC TRUST CO., LTD., Kofu (JP)

(72) Inventors: Tetsuo Maruyama, Kofu (JP); Yoshikazu Kato, Kofu (JP)

(73) Assignee: PATIC TRUST CO., LTD., Kofu (JP)

( * ) Notice: Subject to any disclaimer, the term of this patent is extended or adjusted under 35 U.S.C. 154(b) by 0 days.

(21) Appl. No.: 17/924,171

(22) PCT Filed: Jul. 27, 2021

(86) PCT No.: PCT/JP2021/027810
§ 371 (c)(1),
(2) Date: Nov. 9, 2022

(87) PCT Pub. No.: WO2022/034794
PCT Pub. Date: Feb. 17, 2022

(65) Prior Publication Data
US 2023/0120218 A1    Apr. 20, 2023

(30) Foreign Application Priority Data

Aug. 12, 2020 (JP) .............................. JP2020-136172

(51) Int. Cl.
*G16H 50/80* (2018.01)
*G06F 21/34* (2013.01)

(52) U.S. Cl.
CPC .................................. *G06F 21/34* (2013.01)

(58) Field of Classification Search
CPC ......... G06F 21/34; G06F 21/32; G16H 50/80; G16H 10/65; G06Q 50/20
See application file for complete search history.

(56) References Cited

U.S. PATENT DOCUMENTS 10,628,756 B1   4/2020 Kuper et al.
2002/0011729 A1* 1/2002 Lackey ............... B42D 15/00
                                                283/113
(Continued)

FOREIGN PATENT DOCUMENTS

CN   111062828 A   4/2020
JP   2003-54163 A   2/2003
(Continued)

OTHER PUBLICATIONS

International Search Report dated Nov. 2, 2021 in corresponding application No. PCT/JP2021/027810; 5 pgs.
Written Opinion of the International Search Authority dated Nov. 2, 2021 in corresponding application No. PCT/JP2021/027810; 6 pgs.
(Continued)

*Primary Examiner* — Jeffrey C Pwu
*Assistant Examiner* — William A Corum, Jr.
(74) *Attorney, Agent, or Firm* — Maier & Maier, PLLC

(57) ABSTRACT

A writing apparatus that writes stored information into a chip which has been embedded in an individual being a living body, a reading apparatus that reads the stored information which is stored in the chip, and a management server. The stored information includes at least chip identification information that enables the chip to be distinguished from other chips, and movement history information that includes a movement history of the individual. The movement history is generated on a basis of a zip code and a date and a time of arrival at a predetermined region corresponding to the zip code. The chip identification information and the movement history information are stored in association with each other in the management server.

16 Claims, 8 Drawing Sheets

(56) References Cited

U.S. PATENT DOCUMENTS

2007/0194099 A1* 8/2007 Miller .................. A61B 5/1112
340/572.1
2010/0277283 A1* 11/2010 Burkart ................. G06Q 10/00
340/10.3

FOREIGN PATENT DOCUMENTS

| JP | 2003-284113 A | 10/2003 |
| JP | 2004-295406 A | 10/2004 |
| JP | 2009-129353 A | 6/2009 |
| JP | 2014-27920 A | 2/2014 |
| JP | 2017-4165 A | 1/2017 |
| JP | 2017-70249 A | 4/2017 |
| JP | 2018-533444 A | 11/2018 |
| JP | 6533327 B1 | 6/2019 |
| JP | 2020-515934 A | 5/2020 |

OTHER PUBLICATIONS

Japanese Office Action dated Jan. 20, 2021 in corresponding application No. 2020-136172; 10 pgs. Japanese Office Action dated Jun. 16, 2021 in corresponding application No. 2020-136172; 6 pgs.

Toshiro Hikita et al., "Framework proposal about Trust Points for Location Based Services", SCIS2015, The 32nd Symposium on Cryptography and Information Security, Japan, Jan. 23, 2015, The Institute of Electronics, Information and Communication Engineers, 10 pgs.

"Health Management System Operation Manual: Infant Health Examination Edition", Japan, Oki Electric Industry, Oct. 15, 1999, 1.00 edition, p. 66-88, 25 pgs.

International Preliminary Report on Patentablity dated Feb. 23, 2023, in corresponding International Application No. PCT/JP2021/027810, 5 pages.

\* cited by examiner

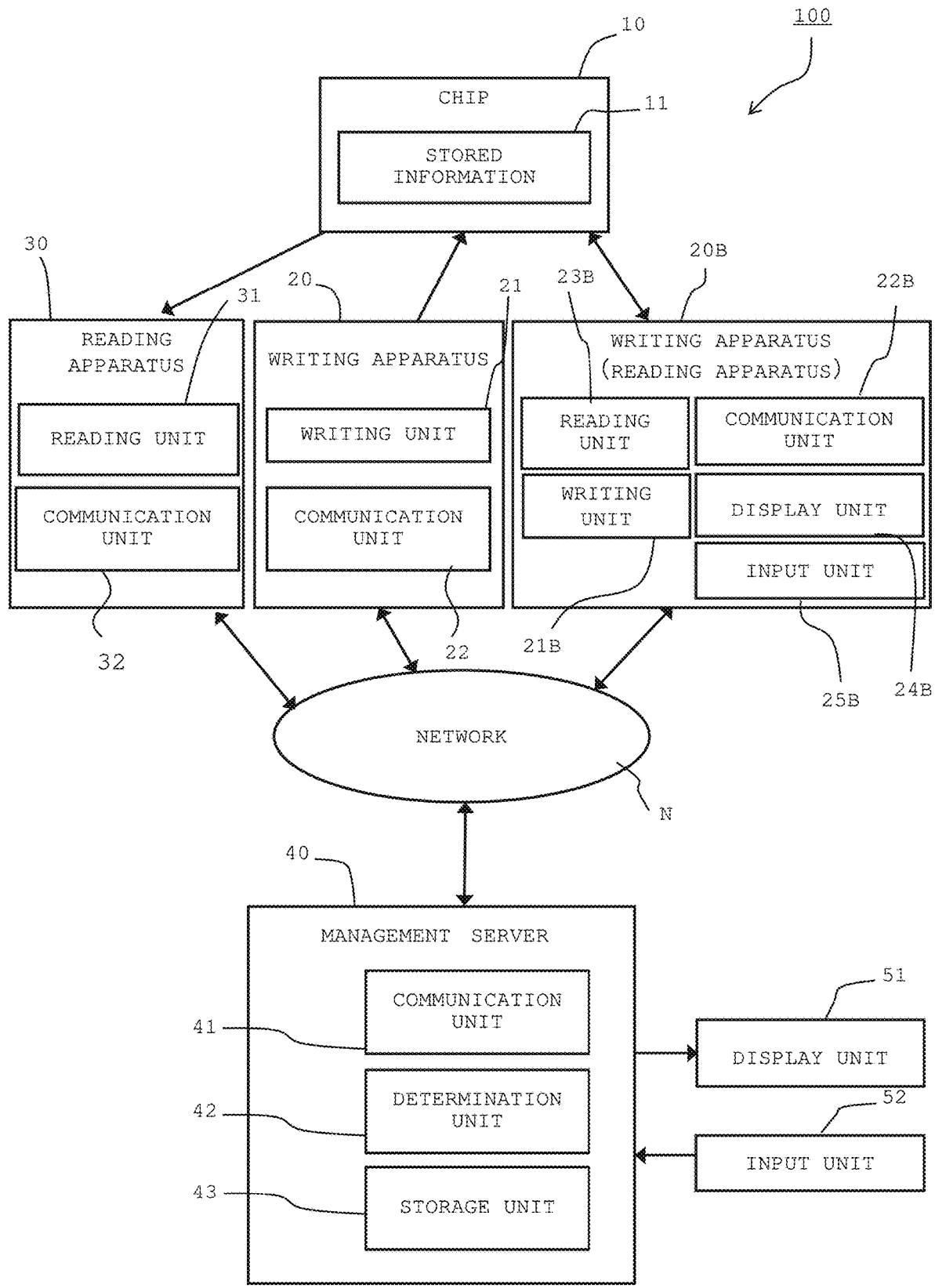
[FIG.1]

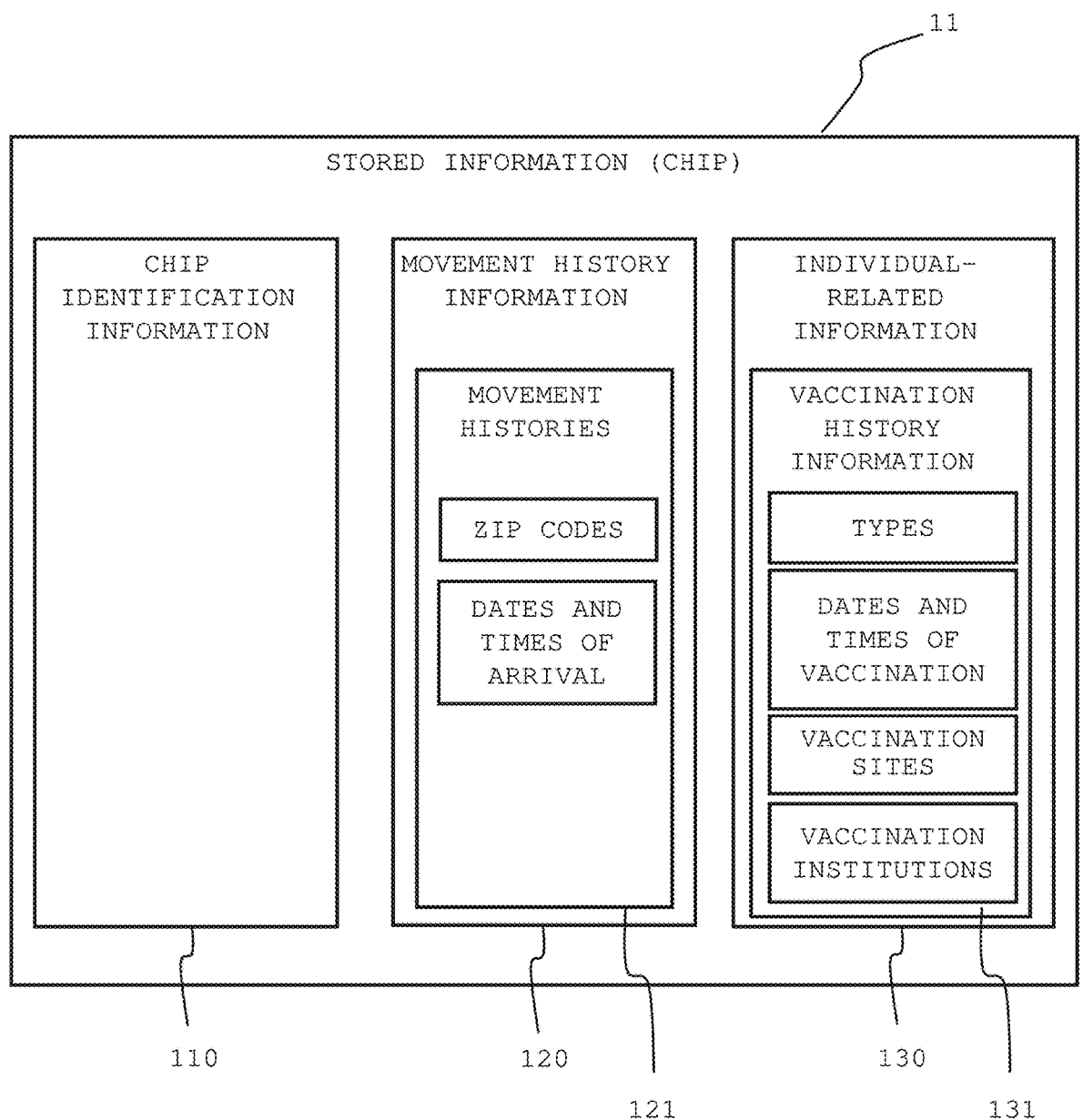
[FIG.2]

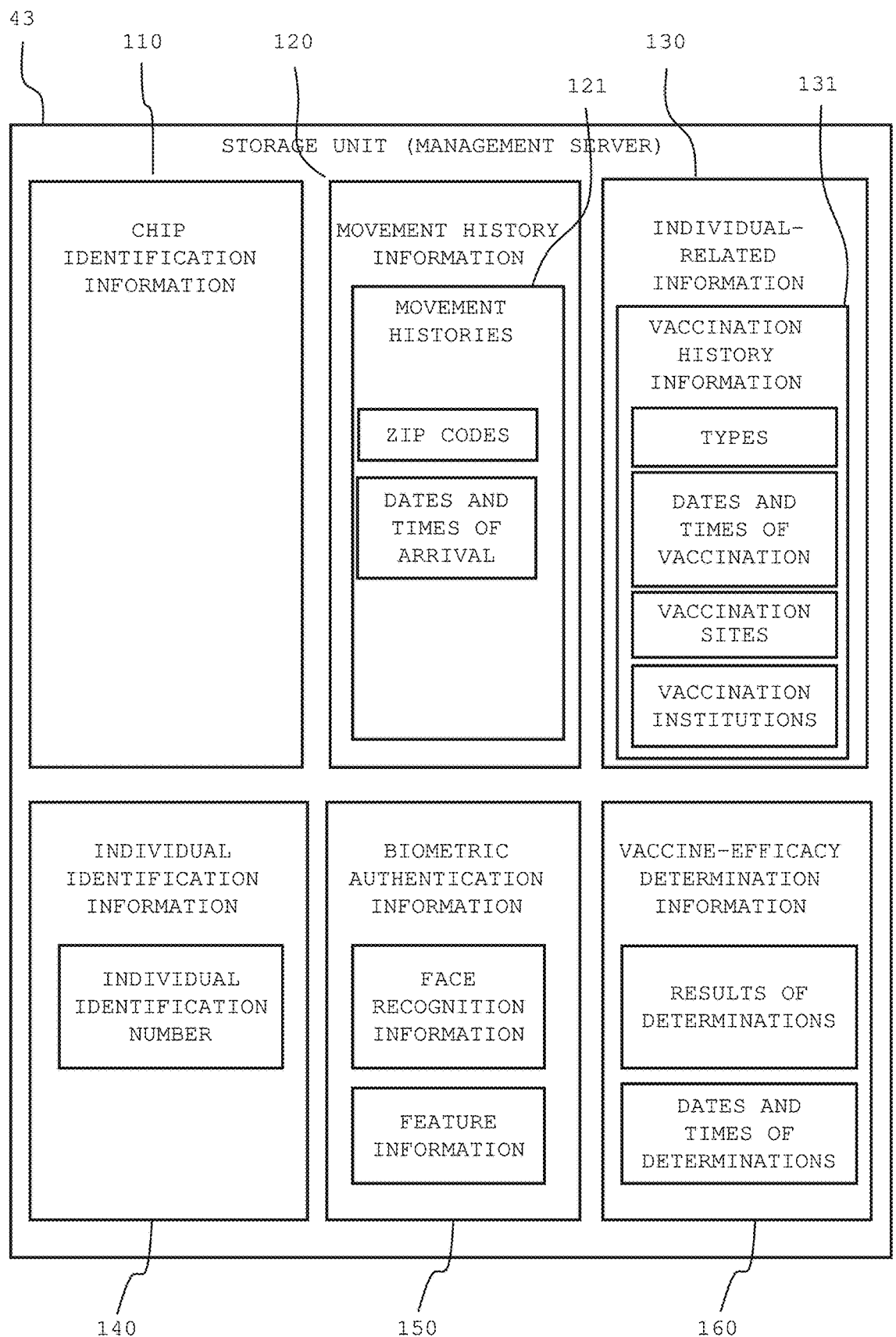

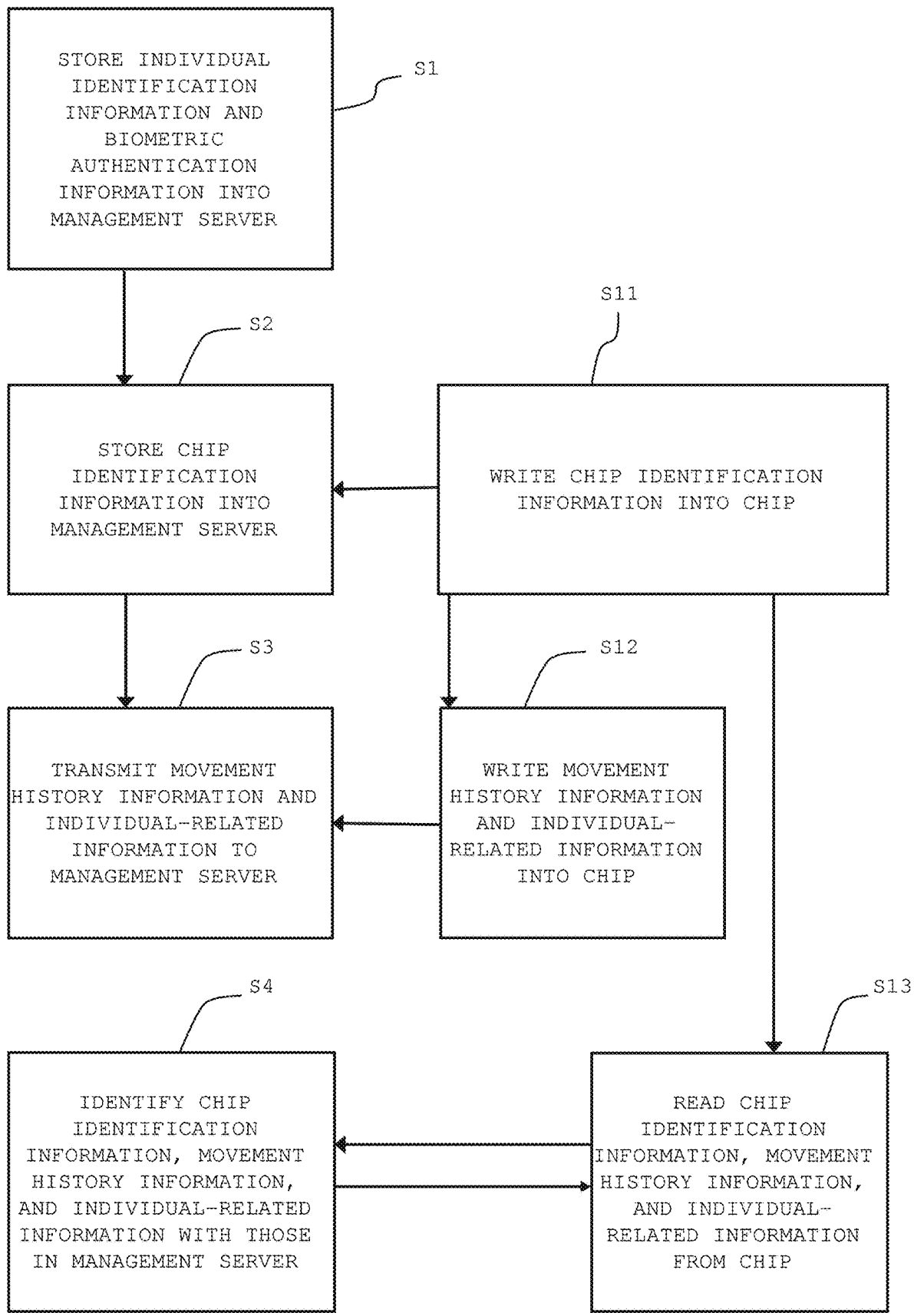

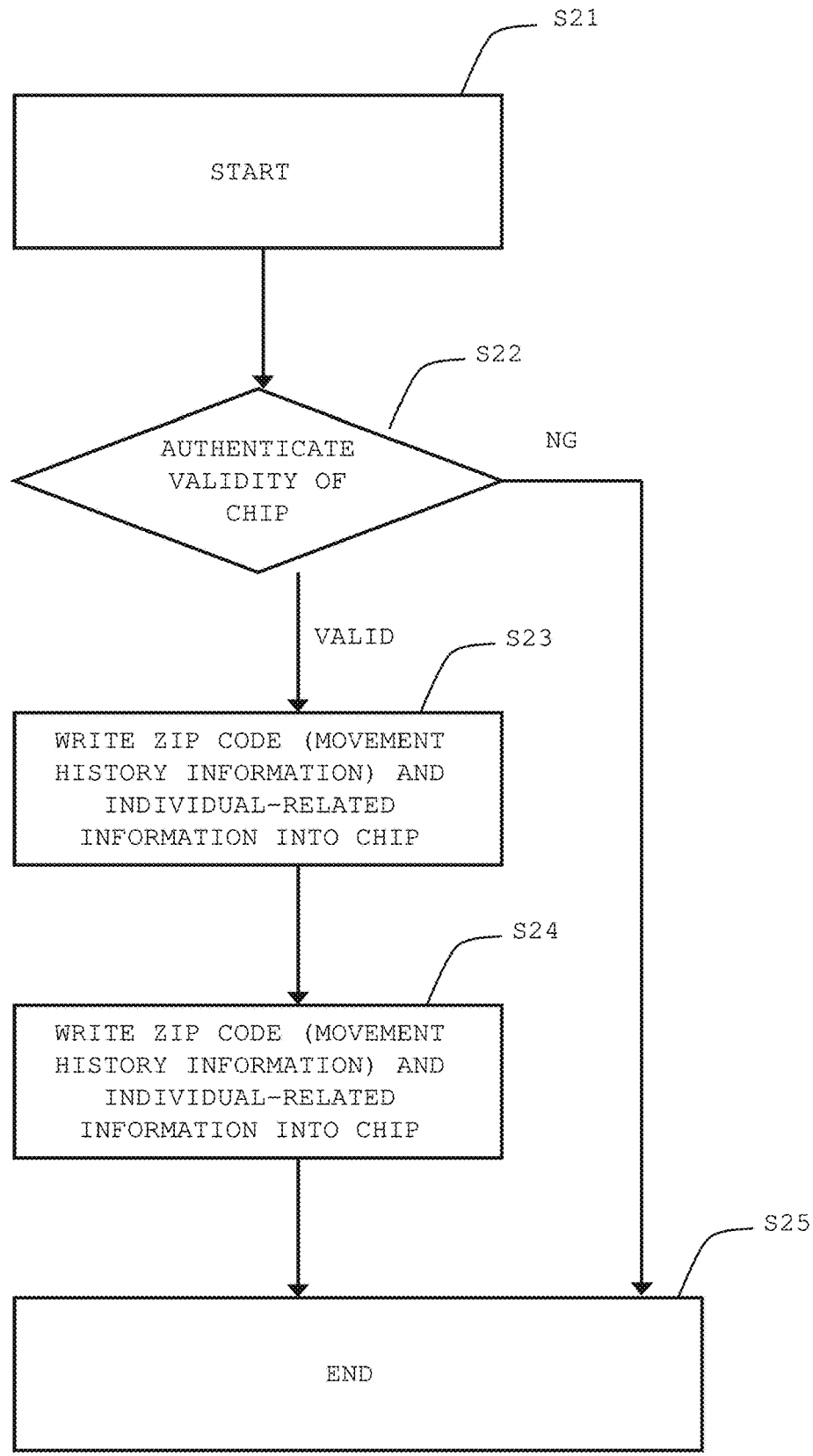
[FIG.5]

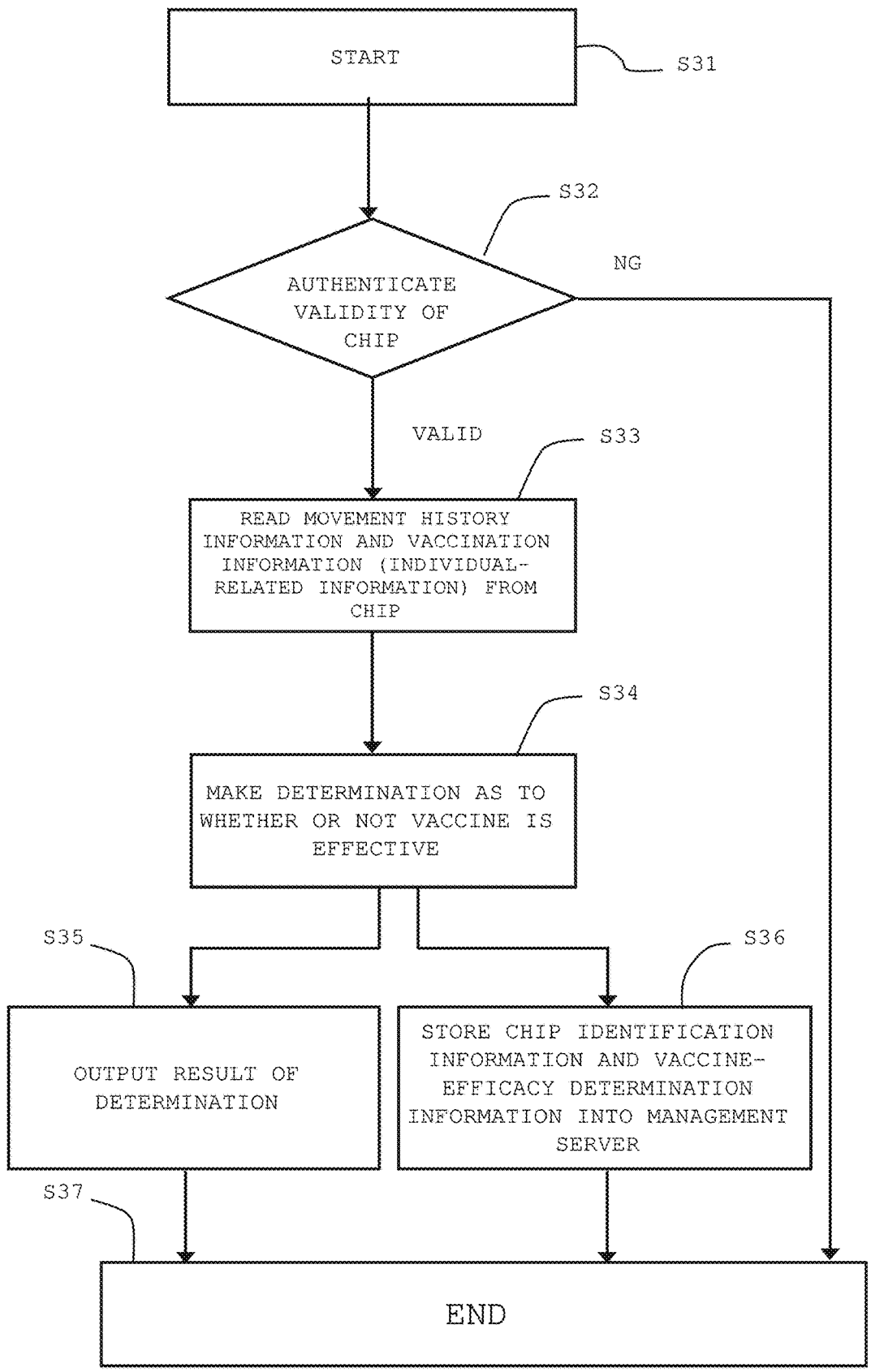

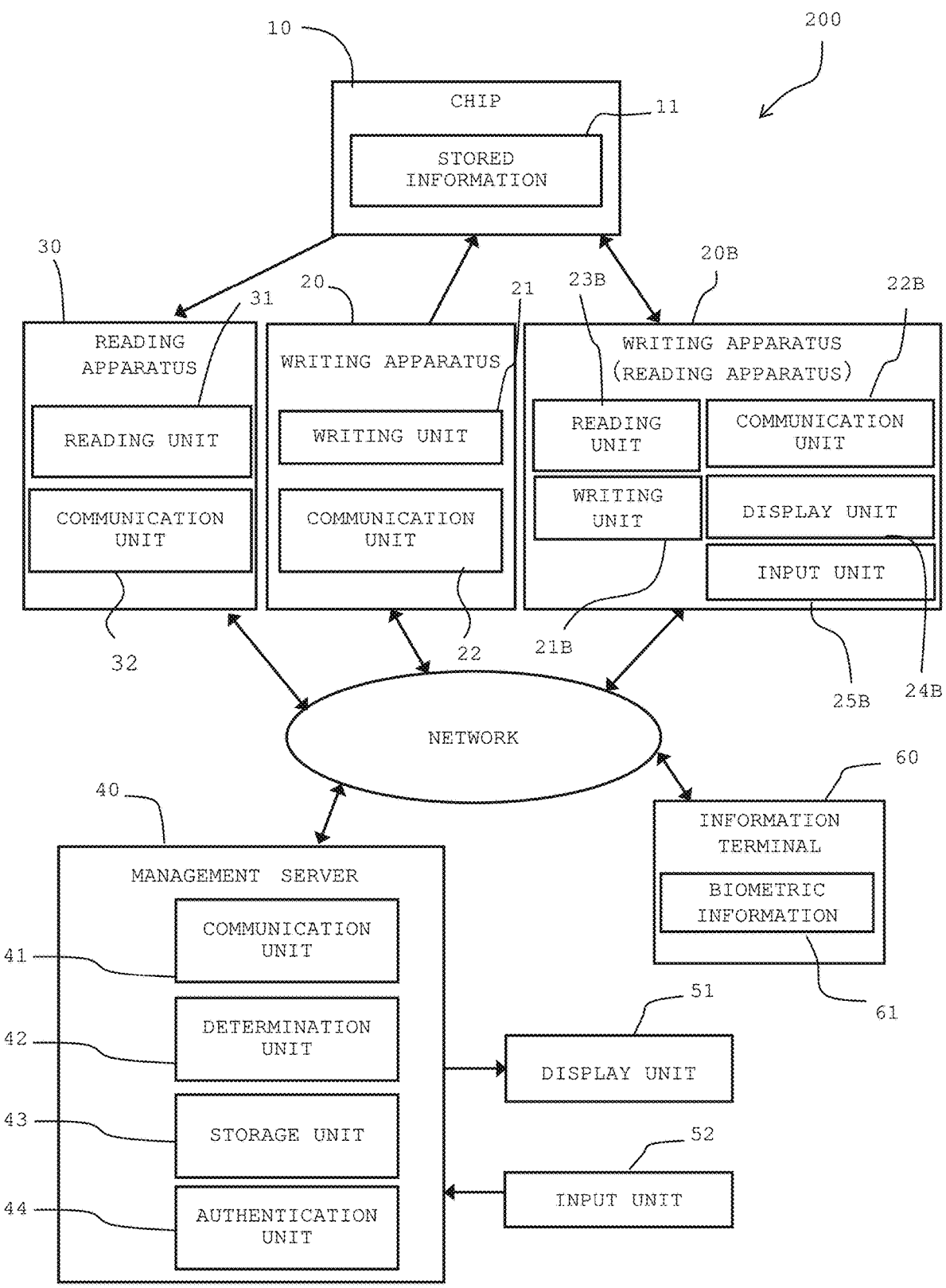
[FIG.7]

[FIG.8]
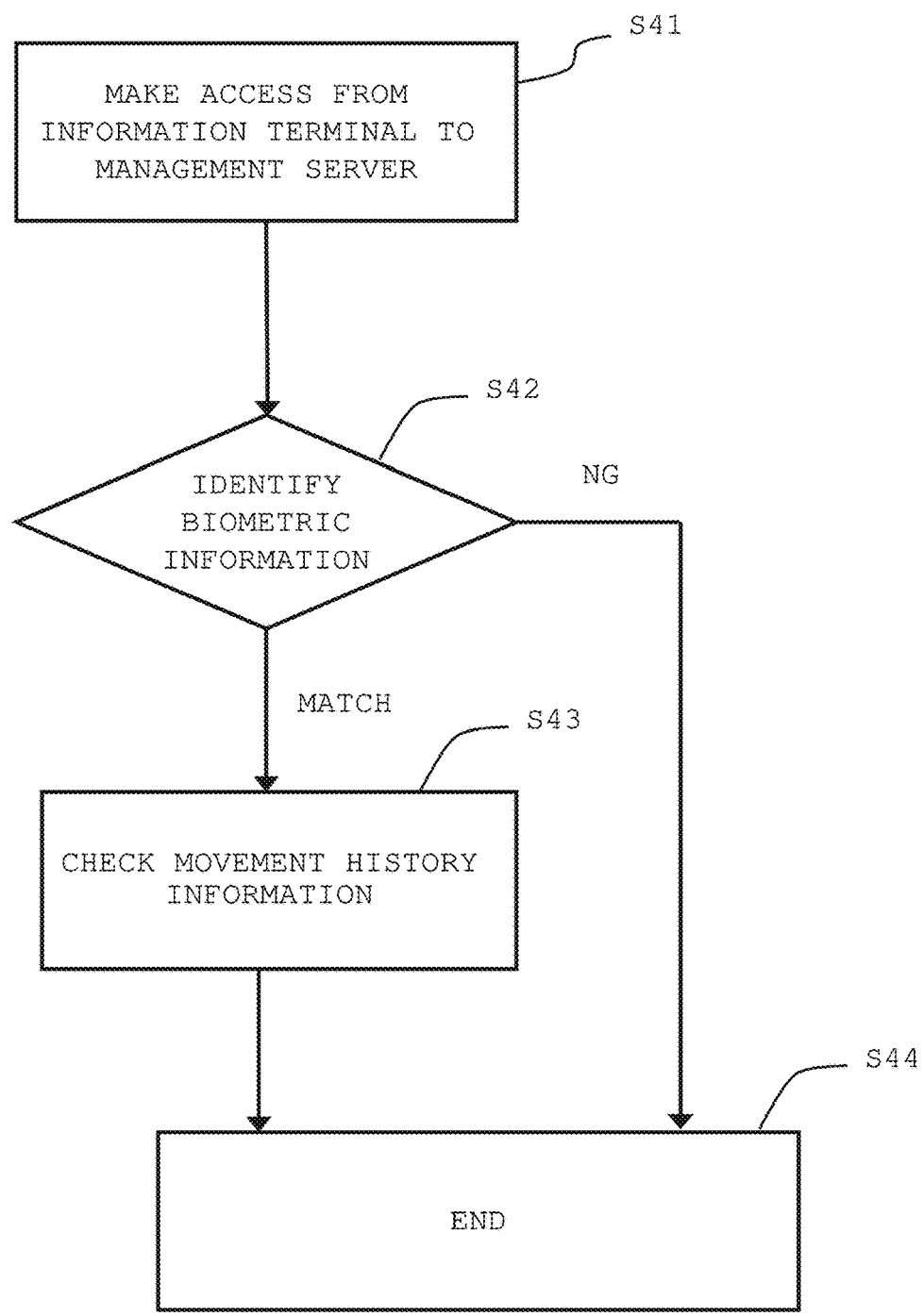

MOVEMENT HISTORY INFORMATION CONFIRMING METHOD, SYSTEM THEREFOR, AND MANAGEMENT SERVER

DESCRIPTION

Technical Field

The present invention relates to a movement-history-information checking method that enables individual-related information such as a vaccination history and enables individual movement-history information to be easily checked at places to stay throughout the world. The present invention relates also to a system and a management server for the movement-history-information checking method.

Background

Vaccination has been performed to prevent infectious diseases and other epidemic diseases such as influenza. In order, for example, to enhance its efficacy, to cope with viral mutations, and to regenerate attenuated antibodies, the vaccination may be performed a plurality of times against the same epidemic disease. In addition, due to the existence of diverse epidemic diseases, the vaccination is performed against each of the epidemic diseases. In view of such circumstances, various methods of reliably recording vaccination histories and enabling these vaccination histories to be easily checked have been proposed (refer, for example, to Japanese Patent Application Laid-open No. 2003-54163 and Japan Patent No. 6533327).

Meanwhile, along with globalization of recent years, the number of people who travel from country to country throughout the world has significantly increased. There have been demands for preventing domestic and international spread of infection by controlling the infection at borders, specifically, by grasping health statuses of inbound persons and outbound persons, and by restricting entry and exit of persons who have been infected with an epidemic disease and have already had symptoms. In addition, even when these persons have not yet had the symptoms at the time of exit and entry, they may be in a latent stage or an early stage of the infection. It is undesirable to overlook the persons in such a state and to allow their entry and exit. In order to prevent entry and exit of such persons, it is significantly important to check at least individual movement-history information, vaccination histories, and efficacy of vaccination.

SUMMARY OF INVENTION

However, the vaccination histories are recorded seldom in a unified format in each country. Even when the vaccination histories are recorded in the unified format, the vaccination histories cannot be easily checked in other countries due to, for example, differences in language or in recording format. In this way, it is significantly difficult to make determinations as to whether or not vaccination is effective.

In addition, with regard to the movement history information of a person to be a target, although information about entry and exit can be checked from record of his/her passport, it is difficult to grasp details of his/her movement histories in each of the countries. Although such a fact that an epidemic disease was prevalent in a specific country or a specific region in a specific period can be specified on the basis of information, for example, from the World Health Organization, it may be difficult, from a viewpoint of, for example, privacy protection, to investigate in detail whether or not a specific inbound person or a specific outbound person stayed in that country or that region in that period.

In addition, protection of information that may be used for specifying an installation location of an apparatus that monitors and records the movement histories of the person to be the target is essential for deterring terrorism.

In view of such circumstances, the present invention has been made to achieve an object to enable movement history information of individuals to be acquired throughout the world while appropriately protecting their privacy, and to enable determinations as to whether or not these individuals are infected with epidemic diseases to be made easily, promptly, and reliably on the basis of their movement history information. In addition, it is another object of the present invention to enable vaccination history information of the individuals to be easily acquired, and to enable the determinations as to whether or not these individuals are infected with epidemic diseases to be made more reliably not only on the basis of their movement history information but also on the basis of their vaccination history information.

In order to achieve the above-mentioned objects, according to the present invention, there is provided a movement-history-information checking method that is implemented by using a chip embedded in a living body, a writing apparatus that writes information into the chip, a reading apparatus that reads the information from the chip, and a management server that manages the information read by the reading apparatus, the chip storing, as stored information, at least chip identification information that enables the chip to be distinguished from other chips, movement history information that includes a movement history of the living body, and vaccination history information about the living body, the movement-history-information checking method including:

a writing step of writing, by the writing apparatus on a movement route of the living body, a zip code of a location where the writing apparatus is installed, and a date and a time of arrival at a predetermined region corresponding to the zip code as the movement history information into the chip; and a determination step of making, by the management server on a basis of the chip identification information, the vaccination history information, and the movement history information that are read from the chip by the reading apparatus, a determination as to whether or not a vaccine administered to the living body corresponding to the chip identification information is effective.

The writing apparatus is preferred to include a first writing apparatus associated with a vaccination institution, and a second writing apparatus installed in a location other than a location of the first writing apparatus, and the writing step is preferred to include a first writing step of writing, by the first writing apparatus, when the living body is vaccinated at the vaccination institution, a zip code of a location of the vaccination institution as the movement history information into the chip, and the vaccination history information about the vaccination into the chip, and a second writing step of writing, by the second writing apparatus, a zip code of the location of the second writing apparatus as the movement history information into the chip.

The vaccination history information is preferred to include
- a type of the vaccine,
- a date and a time when the vaccine is administered,
- a vaccination site, and
- a vaccination institution.

The determination step is preferred to include
making, if a vaccination history is present on a basis of the vaccination history information and the movement history information, a determination as to whether or not the administered vaccine is effective at that time point against a target epidemic disease, and
making, if the vaccination history is absent, a determination as to whether or not the living body has been infected with a predetermined epidemic disease.

The determination step is preferred to include making, if a vaccination history is present, on a basis of the type of the vaccine and the date and the time when the vaccine is administered in the vaccination history information, as the determination as to whether or not the administered vaccine is effective, at least one of
a determination (1) that the administered vaccine is currently effective because antibodies probably have been generated and maintained,
a determination (2) that the administered vaccine is still ineffective because the antibodies have not yet been generated due to an insufficient lapse of a time period since the vaccination, and
a determination (3) that the administered vaccine is not effective because the generated antibodies have been attenuated or disappeared due to a lapse of a considerable time period since the vaccination.

A procedure of the writing by the writing apparatus is preferred to include writing the stored information into the chip when the living body enters for a first time, with the writing apparatus always turned on, an area where wireless communication with the writing apparatus can be performed,
the writing apparatus is preferred to include a sensor that detects approach of the living body, and
the writing procedure is preferred to be executed when the sensor detects the approach of the living body.

According to the present invention, there is provided a movement-history-information checking system including:
a chip embedded in a living body;
a writing apparatus that writes information into the chip; and
a management server that manages the information read by a reading apparatus,
the chip storing, as stored information, at least
  chip identification information that enables the chip to be distinguished from other chips,
  movement history information that includes a movement history of the living body, and
  vaccination history information about the living body,
the writing apparatus on a movement route of the living body writing,
  a zip code of a location where the writing apparatus is installed, and
  a date and a time of arrival at a predetermined region corresponding to the zip code as the movement history information into the chip,
the management server making, on a basis of the chip identification information, the vaccination history information, and the movement history information that are read from the chip by the reading apparatus, a determination as to whether or not a vaccine administered to the living body corresponding to the chip identification information is effective.

The writing apparatus is preferred to include
a first writing apparatus associated with a vaccination institution, and
a second writing apparatus installed in a location other than a location of the first writing apparatus,
the first writing apparatus is preferred to carry out a first writing step of writing, when the living body is vaccinated at the vaccination institution,
  a zip code of a location of the vaccination institution as the movement history information into the chip, and
  the vaccination history information about the vaccination into the chip, and
the second writing apparatus is preferred to carry out a second writing step of writing a zip code of the location of the second writing apparatus as the movement history information into the chip.

The vaccination history information is preferred to include
- a type of the vaccine,
- a date and a time when the vaccine is administered,
- a vaccination site, and
- a vaccination institution.

The management server is preferred to
make, if a vaccination history is present on a basis of the vaccination history information and the movement history information, a determination as to whether or not the administered vaccine is effective at that time point against a target epidemic disease, and
make, if the vaccination history is absent, a determination as to whether or not the living body has been infected with a predetermined epidemic disease.

The management server is preferred to make, if a vaccination history is present, on a basis of the type of the vaccine and the date and the time when the vaccine is administered in the vaccination history information, as the determination as to whether or not the administered vaccine is effective, at least one of
a determination (1) that the administered vaccine is currently effective because antibodies probably have been generated and maintained,
a determination (2) that the administered vaccine is still ineffective because the antibodies have not yet been generated due to an insufficient lapse of a time period since the vaccination, and
a determination (3) that the administered vaccine is not effective because the generated antibodies have been attenuated or disappeared due to a lapse of a considerable time period since the vaccination.

A procedure of the writing by the writing apparatus is preferred to include writing the stored information into the chip when the living body enters for a first time, with the writing apparatus always turned on, an area where wireless communication with the writing apparatus can be performed,
the writing apparatus is preferred to include a sensor that detects approach of the living body, and
the writing procedure is preferred to be executed when the sensor detects the approach of the living body.

According to the present invention, there is provided a management server that is used in a movement-history-information checking method including writing, by a writing apparatus on a movement route of a living body, a zip code of a location where the writing apparatus is installed, and a date and a time of arrival at a predetermined region corresponding to the zip code as movement history information into a chip embedded in the living body and storing, as stored information, at least chip identification information that enables distinction from other chips, the movement history information that includes a movement history of the living body, and vaccination history information about the living body, the management server carrying out an acquisition step of acquiring the chip identification information, the vaccination history information, and the movement history information that are read from the chip by a reading apparatus, and a determination step of making, on a basis of the chip identification information, the vaccination history information, and the movement history information that are acquired in the acquisition step, a determination as to whether or not a vaccine administered to the living body corresponding to the chip identification information is effective.

The vaccination history information is preferred to include a type of the vaccine, a date and a time when the vaccine is administered, a vaccination site, and a vaccination institution.

The determination step is preferred to include making, if a vaccination history is present on a basis of the vaccination history information and the movement history information, a determination as to whether or not the administered vaccine is effective at that time point against a target epidemic disease, and making, if the vaccination history is absent, a determination as to whether or not the living body has been infected with a predetermined epidemic disease.

The determination step is preferred to include making, if a vaccination history is present, on a basis of the type of the vaccine and the date and the time when the vaccine is administered in the vaccination history information, as the determination as to whether or not the administered vaccine is effective, at least one of a determination (1) that the administered vaccine is currently effective because antibodies probably have been generated and maintained, a determination (2) that the administered vaccine is still ineffective because the antibodies have not yet been generated due to an insufficient lapse of a time period since the vaccination, and a determination (3) that the administered vaccine is not effective because the generated antibodies have been attenuated or disappeared due to a lapse of a considerable time period since the vaccination.

Advantageous Effects of Invention

According to the present invention, it is possible to provide a movement-history-information checking system, a movement-history checking method, and a management server that enable movement history information of individuals to be acquired throughout the world while appropriately protecting their privacy, and that enable determinations as to whether or not these individuals are infected with epidemic diseases to be made easily, promptly, and reliably on the basis of their movement history information.

BRIEF DESCRIPTION OF THE DRAWINGS

[FIG. 1] A block diagram showing a configuration of a movement-history-information checking system according to a first embodiment of the present invention.

[FIG. 2] A diagram showing a configuration of data in a chip according to the first embodiment.

[FIG. 3] A diagram showing a configuration of data in a storage unit of a management server according to the first embodiment.

[FIG. 4] A flowchart showing exchange of data (information) between apparatuses in the movement-history-information checking system according to the first embodiment.

[FIG. 5] A flowchart showing a procedure in a writing apparatus according to the first embodiment.

[FIG. 6] A flowchart showing a procedure in a reading apparatus according to the first embodiment.

[FIG. 7] A block diagram showing a configuration of a movement-history-information checking system according to a second embodiment of the present invention.

[FIG. 8] A flowchart showing a procedure of access from an information terminal to the movement-history-information checking system according to the second embodiment.

DETAILED DESCRIPTION OF THE EMBODIMENTS

Below, a movement-history-information checking system, a movement-history checking method, and a movement-history-information checking method according to embodiments of the present invention, and a reading apparatus, a writing apparatus, and chips to be used in these system and methods are described in detail with reference to the drawings.

In this embodiment, living bodies (such as humans) are exemplified as individuals of the present invention. However, these individuals need not necessarily be the living bodies, and may be certificates such as passports.

First Embodiment

As shown in FIG. 1, a movement-history-information checking system 100 includes a writing apparatus 20 that writes stored information 11 into a chip 10, a reading apparatus 30, and a management server 40.

The writing apparatus 20 is a writing device that writes the stored information 11 into the chip 10 embedded in the individual being the living body. As shown in FIG. 2, the stored information 11 includes chip identification information 110 that enables the chip 10 to be distinguished from other chips, movement history information 120 that includes movement histories 121 of the individual, and individual-related information 130 that includes vaccination history information 131 and other information.

The chip 10 is a chip configured to be capable of being embedded in the individual being the living body. For example, a passive RFID (Radio Frequency Identifier) is used so that writing and reading can be performed by wireless communication using electromagnetic waves or radio waves. The chip 10 stores chip identification data that enables the distinction from the other chips (chip identification information 110), movement history data that includes movement histories of the individual in which the chip 10 is embedded (movement history information 120), and individual-related data (individual-related information 130). The living body in which the chip 10 is embedded is the human, a dog, a cat, a bird, a horse, a pig, a head of cattle, or other animals.

The chip identification information 110 includes not only a name of a manufacturer of the chip 10, a model number, and a lot number, but also a serial number that is given to each of the chips 10. Depending, for example, on a scale of manufacture or a system of manufacture of the manufacturer, a name of a manufacturing factory and a date and a time of manufacture may be included.

The individual-related information 130 includes the vaccination history information 131. This vaccination history information 131 includes types of vaccines, dates and times of vaccination, vaccination sites, and vaccination institutions. The types of the vaccines include names of manufacturers and model numbers, and the vaccination sites include names of regions corresponding to zip codes and names of countries. As examples of the vaccination institutions, there may be mentioned a medial institution and an inspection institution.

As shown in FIG. 2, the movement histories 121 included in the movement history information 120 are each generated on the basis of a zip code and of a date and a time of arrival at a predetermined region corresponding to the zip code. The zip code encompasses numbers and letters assigned respectively to regions in each country for sorting mail, such as "postal codes" in English-speaking countries and "ZIP codes" in the United States. In order that the zip codes are reliably distinguished from those in other countries, respective country codes of the countries are preferred to be added to the zip codes in the movement histories 121. By using such zip codes, the movement histories of the individual can be recognized and recorded in an accurate and relatively detailed manner throughout the world. In addition, specification is not performed up to his/her postal address, which is preferred from a viewpoint of privacy protection. Thus, entry barriers to jurisdictional institutions of the countries are easily removed.

As shown in FIG. 1, the writing apparatus 20 includes a writing unit 21 and a communication unit 22. The writing unit 21 writes the chip identification information 110, the movement history information 120, and the individual-related information 130 to be the stored information 11 into the chip 10 embedded in the individual. The communication unit 22 is configured to enable both wireless communication with the chip 10 in writing the information into the chip 10, and wireless communication to a network N.

The writing apparatus 20 includes one or more writing apparatuses 20 that are installed in a region corresponding to one zip code. Although installation locations of the writing apparatuses 20 are not limited in particular, the writing apparatuses 20 are installed, for example, in an airport, the vaccination institution, an institution that inspects, for example, infectious diseases, a public institution such as a public health center, a university, and a railway station. When the movement histories 121 are written a plurality of times into the chip 10 in the region corresponding to the one zip code, depending on, for example, specifications of the chip 10 or specifications of the movement-history-information checking system 100, (1) all movement histories, (2) only the first or the last one of the movement histories, or (3) the first and the last ones of the movement histories may be stored.

The reading apparatus 30 includes a reading unit 31 and a communication unit 32. The reading unit 31 reads the stored information 11 stored in the chip 10 embedded in the individual. The communication unit 32 is configured to enable both wireless communication with the chip 10 in reading the information from the chip 10, and wireless communication to the network N. Although installation locations of the reading apparatus 30 are not limited in particular, the reading apparatus 30 is installed, for example, in an airport, the vaccination institution, an institution that inspects, for example, infectious diseases, a public institution such as a public health center, a university, and a railway station.

The configurations of the writing apparatus 20 and the reading apparatus 30 are a requisite minimum. A procedure of the writing by this writing apparatus 20 includes writing the stored information 11 into the chip 10, for example, when the individual enters for the first time, with the apparatus always turned on, an area where the wireless communication with the apparatus can be performed. Note that, when a sensor that detects approach of the individual to the writing apparatus 20 is provided so that the writing procedure is executed when this sensor detects the approach of the individual, an amount of electricity to be used can be saved.

A procedure of the reading by the reading apparatus 30 includes reading the stored information 11 from the chip 10, for example, when the individual holds a part in which the chip 10 is embedded over the reading apparatus 30 as instructed by staff engaged in immigration control at the airport.

A writing apparatus and a reading apparatus may have a larger number of functions than those of the writing apparatus 20 and the reading apparatus 30 described above, or may be configured to be an apparatus including both a writing unit and a reading unit. For example, as in a writing apparatus 20B (reading apparatus) shown in FIG. 1, a configuration including a writing unit 21B, a communication unit 22B, a reading unit 23B, a display unit 24B, and an input unit 25B also may be employed. The writing unit 21B has functions similar to those of the writing unit 21 of the above-described writing apparatus 20, and the reading unit 23B has functions similar to those of the reading unit 31 of the above-described reading apparatus 30. The communication unit 22B has the functions of both the communication unit 22 of the above-described writing apparatus 20 and the communication unit 32 of the above-described reading apparatus 30. Below, the writing apparatus 20 or the reading apparatus 30 may be described on an assumption of a configuration having functions other than those of the writing unit 21 and the communication unit 22, or functions other than those of the reading unit 31 and the communication unit 32.

The display unit 24B of the writing apparatus 20B is constituted, for example, by a liquid crystal display, and displays information, guidance, and the like about the reading from and the writing into the chip 10 for a target as the individual. During the procedures of the writing and the reading, the input unit 25B is used for input operations for checking the target as the individual or for issuing an instruction, or used for operations such as advancement of the procedures by an operator of the writing apparatus 20B, and communication with the management server 40.

As shown in FIG. 1, the management server 40 is communicable with the writing apparatuses 20 and 20B and the reading apparatus 30 via the network N. This communication is performed via a communication unit 41. The management server 40 includes not only the communication unit 41 but also a determination unit 42 and a storage unit 43. In addition, a display unit 51 on which a predetermined screen is displayed under control by the management server 40, and an input unit 52 for enabling input of data, conditions, and the like for predetermined processes in the management server 40 are connected to the management server 40.

If a vaccination history is present on the basis of the vaccination history information 131 and the movement history information 120, the determination unit 42 makes a determination as to whether or not an administered vaccine is effective at that time point against a target epidemic disease. If the vaccination history is absent, the determination unit 42 makes a determination as to whether or not the individual has been infected with a predetermined epidemic disease.

If the vaccination history is present, the determination unit 42 makes, on the basis of the types of the vaccines and the dates and the times of vaccination in the vaccination history information 131, as the determination as to whether or not the administered vaccine is effective, such a determination (1) that the administered vaccine is currently effective because antibodies probably have been generated and maintained, (2) that the administered vaccine is still ineffective because the antibodies have not yet been generated due to an insufficient lapse of a time period since the vaccination, or (3) that the administered vaccine is not effective because the generated antibodies have been attenuated or disappeared due to a lapse of a considerable time period since the vaccination.

In addition, in the above-described cases of (2) and (3), if the determination unit 42 makes, with reference to the movement history information 120, a determination that the individual has ever stayed, for example, in a region where an infection rate of an epidemic disease is high, the determination unit 42 makes a determination that the individual may be infected. Thus, the individual is suggested or directed to have a test to check whether or not he/she is infected.

Also when the vaccination history is absent, if the determination unit 42 makes, with reference to the movement history information 120, the determination that the individual has ever stayed in the region where the infection rate of the epidemic disease is high, the determination unit 42 makes the determination that the individual may be infected. Thus, the individual is suggested or directed to have the test to check whether or not he/she is infected.

As shown in FIG. 3, in the storage unit 43 of the management server 40, the movement history information 120, the individual-related information 130, individual identification information 140, biometric authentication information 150, and vaccine-efficacy determination information 160 are stored while linked to the chip identification information 110.

As the movement history information 120 and the individual-related information 130, the information that is read from the chip 10 by the reading apparatus 30 is transmitted to the management server 40 via the network N while linked to the chip identification information 110, and then stored into the storage unit 43.

The individual identification information 140, the biometric authentication information 150, and the vaccine-efficacy determination information 160 are directly registered with and stored into the management server 40 after making a determination as to into which of individuals to embed the chip 10 and before performing the writing or the reading. The individual identification information 140, the biometric authentication information 150, and the vaccine-efficacy determination information 160 are input and stored into the storage unit 43 by an operation to the input unit 52. Information necessary for the input operation and the stored information is displayed on the display unit 51.

The vaccine-efficacy determination information 160 includes results of the determinations made by the determination unit 42 as described above, and dates and times of the determinations.

The individual identification information 140 includes an individual identification number shown in FIG. 3 as information that enables the individual to be distinguished from other ones of the individuals. As examples of the individual identification number, in Japan, there may be mentioned an individual number (My Number), a passport number, and a health-insurance card number. In addition, as the individual identification information 140, not only the individual identification number, but also the name, the date of birth, and nationality of the individual may be used.

The biometric authentication information 150 includes face recognition information and feature information. The biometric authentication information 150 is information that is specific to the individual and that enables the individual to be distinguished from other ones of the individuals.

Examples of the face recognition information include an outer shape of the face or the head, an overall shape and a detail shape of each part such as eyes, the nose, the mouth, and ears, arrangements of and relationships between these parts, and a skeletal shape that can be recognized from an external appearance. In addition, the face recognition information may include colors and luminance of the face and irides of the eyes, shapes of eyebrows, a beard, a hairstyle, and ranges occupied by these parts.

The feature information, which may partially overlap with the above-described face recognition information, includes distances between a plurality of feature points set on the face of the individual, proportions of these distances, and a shape formed by connecting the feature points to each other. In addition, the feature information may include not only the information about the face, but also information about a shape of the whole body, or a figure, height, and weight.

With reference to FIG. 4, an overall procedure is described.

In embedding a chip into a body of an individual, the individual identification information 140 and the biometric authentication information 150 are stored into the storage unit 43 of the management server 40 (Step S1). In addition, the chip identification information 110 is also stored into the storage unit 43 of the management server 40 (Step S2). The individual identification information 140, the biometric authentication information 150, and the chip identification information 110 are stored in association with each other. The chip identification information 110 is stored in the chip 10 in advance (Step S11) before being stored into the management server 40 (Step S2). Note that, Steps S1 and S2 may be carried out in a reverse order.

If the individual in which the chip 10 has been embedded moves to reach a location where the writing apparatus 20 is arranged, the writing apparatus 20 writes the movement history information 120 into the chip 10 (Step S12). This writing may be automatically started by the writing apparatus 20 by detection of the arrival of the chip 10, or may be started when the individual himself/herself or the operator performs an operation to start the writing.

If the individual in which the chip 10 has been embedded is vaccinated, at an institution where the vaccination is performed, the movement history information 120 and the vaccination history information 131 as the individual-related information 130 are written into the chip 10 (writing step) (Step S12).

The movement history information 120 and the individual-related information 130 are not only written into the chip 10, but also transmitted from the writing apparatus 20 to the management server 40, and then stored into the storage unit 43 (Step S3). The transmission to the management server 40 is performed by the communication unit 22 of the writing apparatus 20, for example, at the same timing as the writing into the chip 10, or after a lapse of a predetermined time period since the writing.

From the chip 10 embedded in the individual, the movement history information 120 and the individual-related information 130 are read by the reading apparatus 30 while linked to the chip identification information 110 (reading step) (Step S13). The read information is identified with the information stored in the storage unit 43 of the management server 40 (Step S4). If the determination unit 42 of the management server 40 makes, on the basis of this identification, a determination that the writing is not fraudulent, and that the chip identification information 110, the movement history information 120, and the individual-related information 130 stored in the chip 10 are the same as those stored in the storage unit 43 of the management server 40, the determination unit 42 makes, on the basis of the movement history information 120 and the individual-related information 130, the determination as to whether or not the vaccination is effective. A result of the determination is displayed on the display unit 51 connected to the management server 40, and on a display unit that the reading apparatus 30 may include.

In this case, the determination as to whether or not the vaccination is effective is made, for example, as follows. The determination unit 42 specifies, on the basis of the movement history information, countries (or regions) to which the individual has ever been and periods of stays therein (first dates and times of the stays and last dates and times of the stays), and specifies a designated infectious disease that was prevalent during the periods of the stays in the countries. In addition, the determination unit 42 makes a determination as to whether or not the individual was administered with a vaccine that was effective against the specified infectious disease before the individual had entered the countries, and a determination as to whether or not this vaccine was effective during the specified periods of the stays. Then, the determination unit 42 makes a determination that the administered vaccine is effective if a risk of the designated infectious disease is at a predetermined level or lower in all the countries in which the individual has ever stayed, or if the risk of the designated infectious disease is higher than the predetermined level and at the same time the vaccine that was administered to the individual against the infectious disease is effective in all the countries in which the individual has ever stayed.

With reference to FIG. 5, a writing procedure in the writing apparatus 20 is described. This writing procedure corresponds to Step S12 and Step S3 in FIG. 4.

The writing apparatus 20 starts the writing if the individual in which the chip 10 has been embedded reaches the location where the writing apparatus 20 is installed (Step S21). The writing apparatus 20 may automatically start the writing by detecting the arrival of the chip 10, or the individual himself/herself or the operator may start the writing by performing the operation to start the writing.

Then, the writing apparatus 20 performs authentication of validity of the chip 10 to be a target of the writing (Step S22). This authentication is performed at least by reading the chip identification information 110 stored in the chip 10, and by checking an identity with the chip identification information 110 stored in the storage unit 43 of the management server 40.

If the chip 10 is invalid as a result of the authentication, the writing apparatus 20 ends the writing procedure ("NG" in Step S22). Meanwhile, if the chip 10 is valid ("valid" in Step S22), the writing apparatus 20 writes a zip code and a date and a time of the arrival as the movement history information 120 into the chip 10 (Step S23). In addition, when this writing apparatus 20 is installed in a vaccination institution, and vaccination is performed therein, the writing apparatus 20 writes this vaccination as the vaccination history information 131 into the chip 10.

Next, the writing apparatus 20 communicates with the management server 40, and transmits, to the management server 40, the zip code and the date and the time of the arrival as the movement history information 120, and if any, the vaccination history information 131 that are written into the chip 10 (Step S24). After that, the writing apparatus 20 ends the writing procedure at a time point of receiving, from the management server 40, a notification that the received movement-history information 120 and the received vaccination-history information 131 are stored into the storage unit 43 (Step S25).

With reference to FIG. 6, a reading procedure in the reading apparatus 30 is described. This reading procedure corresponds to Step S13 and Step S4 in FIG. 4.

The reading apparatus 30 performs the reading if the individual in which the chip 10 has been embedded reaches a location where the reading apparatus 30 is installed (Step S31). The reading is started, for example, in response to an operation by an inspector at immigration, or is performed when an infection status of the individual needs to be checked.

Then, the reading apparatus 30 performs authentication of the validity of the chip 10 to be the target of the writing (Step S32). This authentication is performed at least by reading the chip identification information 110 stored in the chip 10, and by checking the identity with the chip identification information 110 stored in the storage unit 43 of the management server 40.

If the chip 10 is invalid as a result of the authentication, the reading apparatus 30 ends the reading procedure ("NG" in Step S32). Meanwhile, if the chip 10 is valid ("valid" in Step S32), the reading apparatus 30 reads, from the chip 10, the zip code and the date and the time of the arrival as the movement history information 120, and the vaccination history information 131 as the individual-related information 130 (Step S33).

The movement history information 120 and the individual-related information 130 read by the reading apparatus 30 are transmitted to the management server 40 while linked to the chip identification information 110. Then, the determination unit 42 make the determination as to whether or not the vaccination is effective (Step S34).

A result of the determination in Step S34 described above is output (transmitted) to the reading apparatus 30 (Step S35), and is displayed on the display unit 51 connected to the management server 40. This result is displayed also on the display unit that the reading apparatus 30 may include. In addition, this result of the determination is stored into the storage unit 43 of the management server 40 (Step S36). After these processes are completed, the reading procedure is ended (Step S37).

With the configuration as described above, according to the first embodiment, since zip codes are used as the movement histories, while privacy of an individual (person) can be appropriately protected, regions or countries to which he/she has ever been can be accurately grasped. Thus, a determination as to whether or not the individual (person) is infected with an epidemic disease can be promptly and reliably made. With use of the zip codes, influence of differences in language or in recording format on the movement histories to be generated can be reduced. With this, the vaccination histories can be easily checked. Thus, the infection status of the individual (person) can be immediately grasped, for example, at immigration or in a medical institution, and hence it is possible to promptly take measures such as quarantine and to promptly make contact with insurance authorities. As a result, infection spread can be efficiently prevented.

Second Embodiment

As shown in FIG. 7, a configuration of a movement-history-information checking system 200 according to a second embodiment is different from that of the movement-history-information checking system 100 according to the first embodiment in that the management server 40 further includes an authentication unit 44. In addition, an information terminal 60 is accessible to this movement-history-information checking system 200 via the network N.

Note that, below, the same components as those according to the first embodiment are denoted by the same reference symbols to omit detailed description thereof. In addition, not only the respective procedures in the writing apparatus 20 and the reading apparatus 30, but also processes similar to those according to the first embodiment among processes in an entirety of the movement-history-information checking system 200 are not described in detail.

The information terminal 60 is an electronic device that has a communication function that enables the information terminal 60 and the movement-history-information checking system 200 to communicate with each other via the network N, and that is capable of predetermined arithmetic processes. As examples of the information terminal 60, there may be mentioned portable information terminals such as a smartphone, and a personal computer.

The information terminal 60 is capable of storing biometric information 61 corresponding to the biometric authentication information 150, or of allowing the biometric information 61 corresponding to the biometric authentication information 150 to be input thereto with use of an input function or an imaging function. Further, the information terminal 60 is also capable of storing information corresponding to the individual identification information 140, or of allowing such information to be input thereto. This information enables support in authentication based on the biometric information 61, or enables authentication without the biometric information 61. Still further, when the chip identification information 110 is stored in the information terminal 60 in advance, the authentication based on the biometric information 61 can be supported thereby and reliably performed.

The authentication unit 44 identifies the biometric authentication information 150 stored in the storage unit 43 of the management server 40 and the biometric information 61 transmitted from the information terminal 60 to the management server 40 with each other. With this, the authentication unit 44 authenticates whether or not a user of the information terminal 60 is an individual corresponding to the biometric authentication information 150.

With reference to FIG. 8, processes of the authentication by the authentication unit 44 and processes after the authentication are described.

First, access is made from the information terminal 60 to the management server 40 via the network N (Step S41). In response, the management server 40 requests the information terminal 60 to transmit the biometric information 61. In addition, the management server 40 also requests the individual identification information 140 and the chip identification information 110 that the information terminal 60 may include.

If the biometric information 61 is transmitted from the information terminal 60, the authentication unit 44 of the management server 40 identifies the face recognition information and the feature information of the biometric authentication information 150 stored in the storage unit 43 and the biometric information 61 with each other (identification step) (Step S42).

If the authentication unit 44 makes, as a result of the identification, a determination that the biometric information 61 transmitted from the information terminal 60 does not match the face recognition information or the feature information of the biometric authentication information 150 stored in the storage unit 43 under predetermined conditions, the authentication unit 44 denies the access from the information terminal 60 to the management server 40, and then ends the authentication procedure (Step S44).

If the authentication unit 44 makes, as the result of the identification (Step S42), a determination that the biometric information 61 transmitted from the information terminal 60 and the face recognition information and the feature information of the biometric authentication information 150 stored in the storage unit 43 match each other under the predetermined conditions, the authentication unit 44 authenticates access to the movement history information 120, the individual-related information 130, the chip identification information 110, the individual identification information 140, and the vaccine-efficacy determination information 160 that are stored in the storage unit 43 of the management server 40 so that these information items can be checked on the information terminal 60 (information checking step) (Step S43).

Note that, as the information that is accessible from the information terminal 60, for example, among the movement history information 120, the individual-related information 130, the chip identification information 110, the individual identification information 140, and the vaccine-efficacy determination information 160, only the movement history information 120 may be set to be accessible in accordance with, for example, security standards of each country.

According to the configuration described hereinabove, the access to the management server 40 can be made from the information terminal 60 if a condition that the biometric information matches the biometric authentication information 150 is satisfied. With this, an individual (person) in which a chip has been embedded is allowed to check the movement history information 120 and the individual-related information 130 of his/her own.

Note that, other functions, advantages, and modifications are similar to those according to the first embodiment.

In addition, for example, whether or not authorization to perform the reading from and the writing into the chip 10 needs to be issued differs from content to content. The writing for updating information into the chip 10 is performed via a management center (bidirectionally). Whether or not authorization to directly read information from the chip 10 is issued depends on the content of the information.

In this embodiment, for example, unique apparatus-identification information (unique information that enables individuals to be distinguished from each other, such as a serial number, more specifically, the name of a manufacturer, a date of manufacture, and a destination of shipping) is given to each of the reading apparatus 30 and the writing apparatus 20. In other words, not only the chip identification information of the chip 10, but also the apparatus identification information of the reading apparatus 30 and the writing apparatus 20 are approved by an appropriate organization, and collectively managed by the management server 40 (central server).

In addition, in the reading apparatus 30, locations are automatically developed on the basis of the zip codes read from the chip 10 so that determinations as to whether or not movements are restricted are automatically made.

Note that, apparatus identification numbers of, for example, the reading apparatus 30 and the writing apparatus 20 are linked to zip codes where these apparatuses are installed. With this, movement histories of living bodies in which the chips 10 have been embedded are generated.

When, for example, the reading apparatus 30 and the writing apparatus 20 access the chip 10, the zip codes of these apparatuses are written as the movement histories. By writing the zip codes of, for example, the reading apparatus 30 and the writing apparatus 20 instead of their specific locations in this way, the installation locations of these apparatuses can be avoided from being specified and from being used for terrorism.

Instead of the one management server 40, a plurality of management servers 40 may be provided, A municipality or a country to which a zip code that is used in initially registering an individual belongs should have a master. In addition, a blockchain and the like may be used to share his/her histories, for example, with another municipality to which a zip code of a destination belongs so as to reduce a risk of tampering.

In addition, in this embodiment, the reading apparatus 30 and the writing apparatus 40 may each include a storage unit so as to store histories of access (reading/writing) to the chip 10.

Reference Signs List 10 chip
11 stored information
20, 20B writing apparatus
21, 21B writing unit
22, 22B communication unit
23B reading unit
24B display unit
25B input unit
30, 20B reading apparatus
31 reading unit
32 communication unit
40 management server
41 communication unit
42 determination unit
43 storage unit
44 authentication unit
51 display unit
52 input unit
60 information terminal
61 biometric information
100 movement-history-information checking system
110 chip identification information
120 movement history information
121 movement history
130 vaccination history information
140 individual identification information
150 biometric authentication information
160 vaccine-efficacy determination information
200 movement-history-information checking system
N network

The invention claimed is:

1. A movement-history-information checking method that is implemented by
a chip embedded in a living body,
a writing apparatus that writes information into the chip,
a reading apparatus that reads the information from the chip, and
a management server that manages the information read by the reading apparatus,
the chip storing, as stored information, at least
chip identification information that enables the chip to be distinguished from other chips,
movement history information that includes a movement history of the living body, and
vaccination history information about the living body, the movement-history-information checking method comprising:
a writing step of writing, by the writing apparatus on a movement route of the living body,
a zip code of a location where the writing apparatus is installed, and
a date and a time of arrival at a predetermined region corresponding to the zip code as the movement history information into the chip; and the method comprising:
a determination step of making, by the management server on a basis of the chip identification information, the vaccination history information, and the movement history information that are read from the chip by the reading apparatus, a determination as to whether or not a vaccine administered to the living body corresponding to the chip identification information is effective.

2. The movement-history-information checking method according to claim 1,
wherein the writing apparatus includes
a first writing apparatus associated with a vaccination institution, and
a second writing apparatus installed in a location other than a location of the first writing apparatus, and
wherein the writing step includes
a first writing step of writing, by the first writing apparatus, when the living body is vaccinated at the vaccination institution,
a zip code of a location of the vaccination institution as the movement history information into the chip, and
the vaccination history information about the vaccination into the chip, and
a second writing step of writing, by the second writing apparatus, a zip code of the location of the second writing apparatus as the movement history information into the chip.

3. The movement-history-information checking method according to claim 1,
wherein the vaccination history information includes
a type of the vaccine,
a date and a time when the vaccine is administered,
a vaccination site, and
a vaccination institution.

4. The movement-history-information checking method according to claim 1,
wherein the determination step comprises:
making, if a vaccination history is present on a basis of the vaccination history information and the movement history information, a determination as to whether or not the administered vaccine is effective at that time point against a target epidemic disease, and
making, if the vaccination history is absent, a determination as to whether or not the living body has been infected with a predetermined epidemic disease.

5. The movement-history-information checking method according to claim 3,
wherein the determination step further comprises: making, if a vaccination history is present, on a basis of the type of the vaccine and the date and the time when the vaccine is administered in the vaccination history information, as the determination as to whether or not the administered vaccine is effective, at least one of
a determination (1) that the administered vaccine is currently effective because antibodies probably have been generated and maintained,
a determination (2) that the administered vaccine is still ineffective because the antibodies have not yet been generated due to an insufficient lapse of a time period since the vaccination, and
a determination (3) that the administered vaccine is not effective because the generated antibodies have been attenuated or disappeared due to a lapse of a considerable time period since the vaccination.

6. The movement-history-information checking method according to claim 1,
wherein a procedure of the writing by the writing apparatus includes writing the stored information into the chip when the living body enters for a first time, with the writing apparatus always turned on, an area where wireless communication with the writing apparatus can be performed,
wherein the writing apparatus includes a sensor that detects approach of the living body, and
wherein the writing procedure is executed when the sensor detects the approach of the living body.

7. A movement-history-information checking system, comprising:
a chip embedded in a living body;
a writing apparatus that writes information into the chip; and
a management server that manages the information read by a reading apparatus,
the chip storing, as stored information, at least
chip identification information that enables the chip to be distinguished from other chips,
movement history information that includes a movement history of the living body, and
vaccination history information about the living body,
the writing apparatus on a movement route of the living body writing,
a zip code of a location where the writing apparatus is installed, and
a date and a time of arrival at a predetermined region corresponding to the zip code as the movement history information into the chip,
wherein the management server makes, on a basis of the chip identification information, the vaccination history information, and the movement history information that are read from the chip by the reading apparatus, a determination as to whether or not a vaccine administered to the living body corresponding to the chip identification information is effective.

8. The movement-history-information checking system according to claim 7,
wherein the writing apparatus includes
a first writing apparatus associated with a vaccination institution, and
a second writing apparatus installed in a location other than a location of the first writing apparatus,
wherein the first writing apparatus carries out a first writing step of writing, when the living body is vaccinated at the vaccination institution,
a zip code of a location of the vaccination institution as the movement history information into the chip, and
the vaccination history information about the vaccination into the chip, and
wherein the second writing apparatus carries out a second writing step of writing a zip code of the location of the second writing apparatus as the movement history information into the chip.

9. The movement-history-information checking system according to claim 7,
wherein the vaccination history information includes
a type of the vaccine,
a date and a time when the vaccine is administered,
a vaccination site, and
a vaccination institution.

10. The movement-history-information checking system according to claim 7,
wherein the management server
makes, if a vaccination history is present on a basis of the vaccination history information and the movement history information, a determination as to whether or not the administered vaccine is effective at that time point against a target epidemic disease, and
makes, if the vaccination history is absent, a determination as to whether or not the living body has been infected with a predetermined epidemic disease.

11. The movement-history-information checking system according to claim 9,
wherein the management server makes, if a vaccination history is present, on a basis of the type of the vaccine and the date and the time when the vaccine is administered in the vaccination history information, as the determination as to whether or not the administered vaccine is effective, at least one of
a determination (1) that the administered vaccine is currently effective because antibodies probably have been generated and maintained,
a determination (2) that the administered vaccine is still ineffective because the antibodies have not yet been generated due to an insufficient lapse of a time period since the vaccination, and
a determination (3) that the administered vaccine is not effective because the generated antibodies have been attenuated or disappeared due to a lapse of a considerable time period since the vaccination.

12. The movement-history-information checking system according to claim 7,
- wherein a procedure of the writing by the writing apparatus includes writing the stored information into the chip when the living body enters for a first time, with the writing apparatus always turned on, an area where wireless communication with the writing apparatus can be performed,
- wherein the writing apparatus includes a sensor that detects approach of the living body, and
- wherein the writing procedure is executed when the sensor detects the approach of the living body.

13. A management server that is used in a movement-history-information checking method including writing, by a writing apparatus on a movement route of a living body,
- a zip code of a location where the writing apparatus is installed, and
- a date and a time of arrival at a predetermined region corresponding to the zip code as movement history information into a chip embedded in the living body and storing, as stored information, at least
- chip identification information that enables distinction from other chips,
- the movement history information that includes a movement history of the living body, and
- vaccination history information about the living body,
- the management server carrying out
  - an acquisition step of acquiring
    - the chip identification information,
    - the vaccination history information, and
    - the movement history information that are read from the chip by a reading apparatus, and
  - a determination step of making, on a basis of the chip identification information, the vaccination history information, and the movement history information that are acquired in the acquisition step, a determination as to whether or not a vaccine administered to the living body corresponding to the chip identification information is effective.

14. The management server according to claim 13, wherein the vaccination history information includes
- a type of the vaccine,
- a date and a time when the vaccine is administered,
- a vaccination site, and
- a vaccination institution.

15. The management server according to claim 13, wherein the determination step includes
- making, if a vaccination history is present on a basis of the vaccination history information and the movement history information, a determination as to whether or not the administered vaccine is effective at that time point against a target epidemic disease, and
- making, if the vaccination history is absent, a determination as to whether or not the living body has been infected with a predetermined epidemic disease.

16. The management server according to claim 14, wherein the determination step includes making, if a vaccination history is present, on a basis of the type of the vaccine and the date and the time when the vaccine is administered in the vaccination history information, as the determination as to whether or not the administered vaccine is effective, at least one of
- a determination (1) that the administered vaccine is currently effective because antibodies probably have been generated and maintained,
- a determination (2) that the administered vaccine is still ineffective because the antibodies have not yet been generated due to an insufficient lapse of a time period since the vaccination, and
- a determination (3) that the administered vaccine is not effective because the generated antibodies have been attenuated or disappeared due to a lapse of a considerable time period since the vaccination.

* * * * *